United States Patent [19]

Terry, Jr.

[11] Patent Number: 4,979,511
[45] Date of Patent: Dec. 25, 1990

[54] STRAIN RELIEF TETHER FOR IMPLANTABLE ELECTRODE

[75] Inventor: Reese S. Terry, Jr., Houston, Tex.

[73] Assignee: Cyberonics, Inc., Houston, Tex.

[21] Appl. No.: 431,095

[22] Filed: Nov. 3, 1989

[51] Int. Cl.$^5$ .......................... A61B 5/04; A61N 1/05
[52] U.S. Cl. .................................... 128/642; 120/784; 120/785
[58] Field of Search ........... 128/784, 785, 786, 419 C, 128/642

[56] References Cited

U.S. PATENT DOCUMENTS

| | | |
|---|---|---|
| 1,968,884 | 8/1934 | Gilbert . |
| 1,979,756 | 11/1934 | McNamee . |
| 2,611,368 | 9/1952 | Pecora ................................. 128/644 |
| 3,449,103 | 3/1970 | Pearce . |
| 3,547,104 | 12/1970 | Buffington ........................... 128/639 |
| 3,724,467 | 4/1973 | Avery et al. ......................... 128/784 |
| 3,779,494 | 12/1973 | Nicholson ............................. 248/50 |
| 3,951,504 | 4/1976 | Clark . |
| 4,046,141 | 9/1977 | DeLuca ................................ 128/642 |
| 4,072,388 | 2/1978 | Dunn ................................ 339/103 R |
| 4,276,882 | 7/1981 | Dickhudt et al. ............... 128/784 X |
| 4,332,257 | 6/1982 | Ayer ..................................... 128/640 |
| 4,573,481 | 3/1986 | Bullars ................................. 128/784 |
| 4,590,946 | 5/1986 | Loeb .................................... 128/642 |
| 4,768,974 | 10/1987 | Zabara ................................. 128/421 |
| 4,774,967 | 10/1988 | Zanakis et al. ...................... 128/785 |
| 4,867,164 | 9/1989 | Zabara ................................. 128/421 |

Primary Examiner—Lee S. Cohen
Attorney, Agent, or Firm—Pravel, Gambrell, Hewitt, Kimball & Krieger

[57] ABSTRACT

An implantable, flexible, helical electrode strcuture is disclosed having an improved connector for attaching the lead wires to the nerve bundle, thereby minimizing damage which might otherwise occur to the contact points between the lead wires and helical electrode.

6 Claims, 1 Drawing Sheet

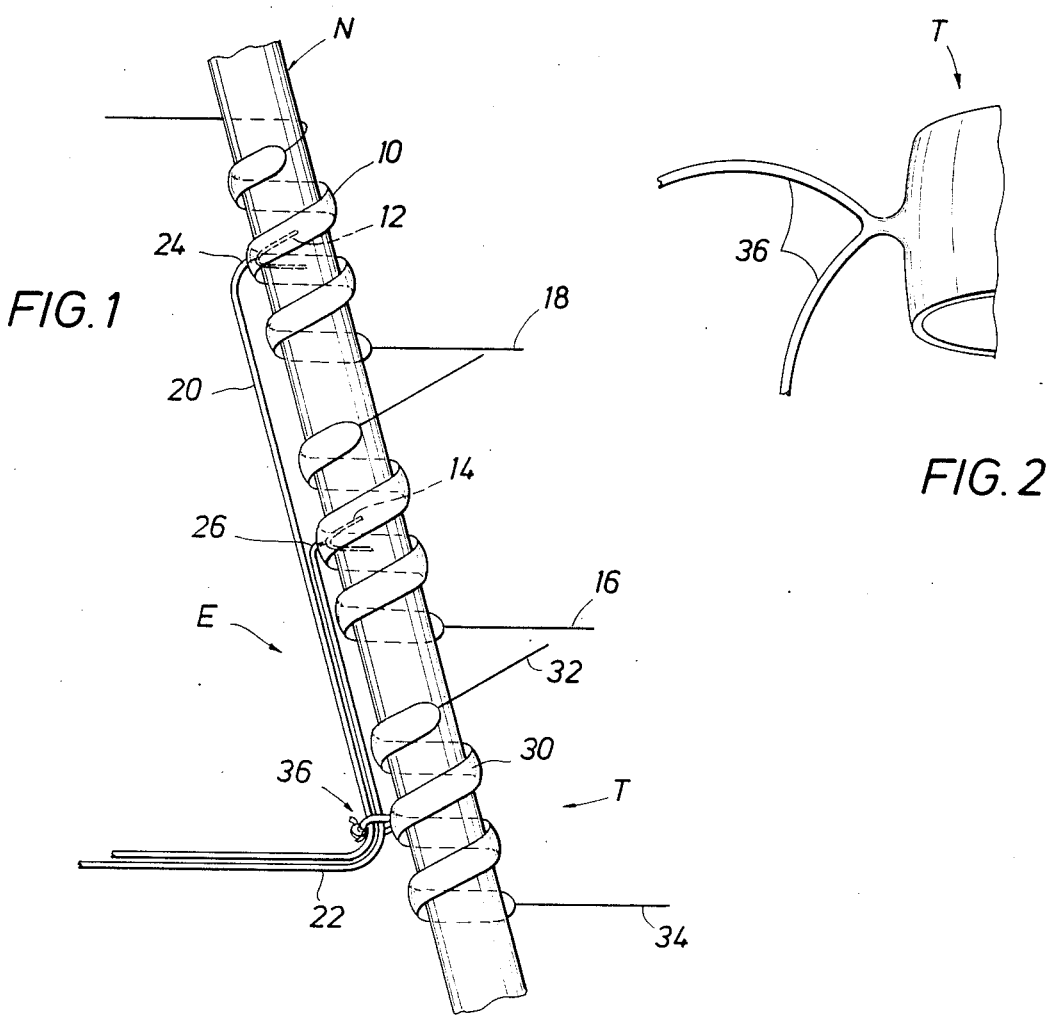
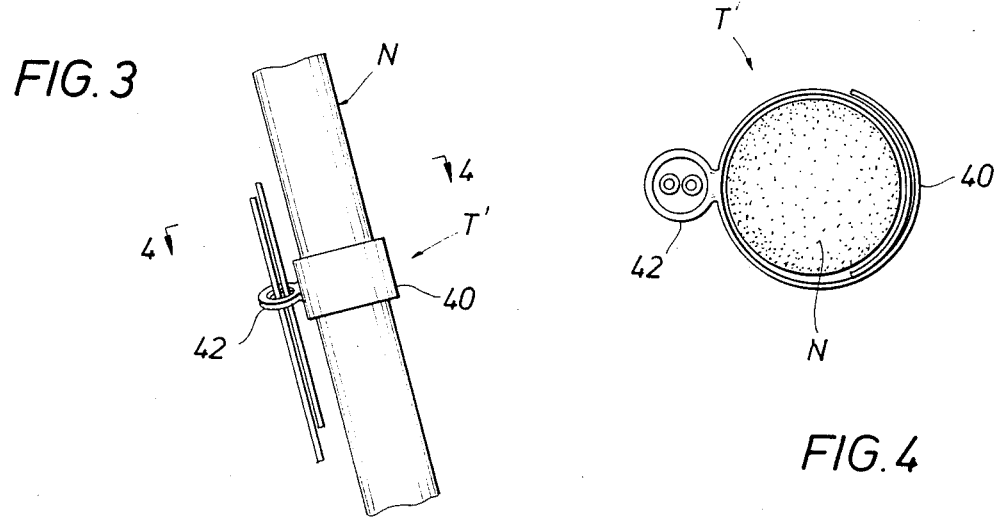

STRAIN RELIEF TETHER FOR IMPLANTABLE ELECTRODE

BACKGROUND OF THE INVENTION

1. Field of the Invention

This invention relates to electrode systems which can be surgically implanted in the human body and attached to nerve bundles to provide stimulation for those nerves as a means for treating nervous system disorders such as seizures or for other purposes relating to diagnostic or therapeutic techniques.

2. Discussion of the Related Art

The use of electrical pulse stimulation of human peripheral nervous system elements has become an important area of research and practical application for both diagnostic and therapeutic techniques. Implanted electrodes have long been used in the field of cardiac pacemaker implants to monitor and control irregular heartbeat and other cardiac related disorders. More recently, implantable electrodes have been used in humans to treat neurological disorders stemming from paralysis, spasms and other dysfunctional states of organs innervated by certain nerve bundles.

Other applications for implantable electrodes relate to their use as recording devices to monitor nervous system activity and in certain instances to provide electrical pulse stimulation in response to such sensed activity.

One further application, as described in U.S. Pat. No. 4,702,254, relates to the periodic stimulation of the vagal nerve to reduce or eliminate seizure disorders such as are associated with epilepsy.

Due to the nature of the electrical activity associated with nerve action, and the need to provide closely coupled, spaced apart electrodes which surround the target nerve bundle, electrodes with a wound helical structure were developed. One such electrode construction is disclosed in U.S. Pat. No. 4,590,946. Electrodes of this design provide a pair of electrode contacts embedded in the inner face of a flexible, helically wound substrate material. In these helical electrodes, the conductors or contacts are connected to an electrical source for monitoring or providing electrical stimulation by one or more pairs of lead wires.

Due to the intricacy of the implant surgery involved, it is necessary that implantable electrodes be relatively easy to attach and conform to the shape of the target nerve bundle. The helical electrode construction has proven to be particularly suitable in that it can be implanted by applying it to the nerve with a corkscrewing action and its spring-like structure naturally conforms to the outer surface of the nerve bundle. These electrodes are necessarily delicate, however, and care must be taken to adequately secure the electrodes to the nerve bundle without effecting the electrode's performance.

Typically, implantable electrodes are helically wound with an inner diameter of approximately 2 mm and an individual helix length of about 3.5 mm, with an overall helix length of 14 mm and total electrode length of 40 cm. The helical substrate is composed of biocompatible silicone rubber and the electrode elements are formed of platinum ribbon which is in some cases only 0.0001 inches thick. The lead wires attach to the electrode elements. The lead wires are typically stainless steel with silicone rubber insulation. The lead wires are attached to the electrode elements with a solder or weld connection.

Implanted electrodes are made of flexible resilient material to accommodate the movement of the nerve bundle itself and the movement of the nerve bundle relative to surrounding tissue. Since the electrode lead wires are attached to the nerve via the electrode structure but also engage the surrounding tissue, any relative movement between the nerve bundle and the surrounding tissue imparts strain on the junction between the lead wires and the helical electrode, and on the nerve itself. Any mechanical forces transmitted to the nerve via the lead wires can cause damage to the nerve or dislocation of the electrode.

To alleviate this problem, prior electrode systems have used a variety of strain-relief elements. U.S. Pat. No. 4,590,946 disclosed a helical electrode with a strain relief tab which was formed around the lead wires and anchored to body tissue such as bone, fascia or other tissue by screws, sutures or other surgical fasteners. While this configuration may have relieved strain imposed by remote forces acting on the lead wires, it did not alleviate the strain on the lead wire to electrode junction which occurred as a result of movement of the nerve relative to the anchoring tissue.

U.S. Pat. No. 4,394,866 disclosed an atrial pacemaker design wherein the lead wires were ligated in place by attachment to an adjacent vein. This design also failed to alleviate strain on the lead wire junction which resulted from relative movement of the anchoring tissue vis-a-vis the electrode implant site.

SUMMARY OF THE INVENTION

The present invention provides a novel implantable flexible helical electrode structure which is particularly suited for attachment to human peripheral nerve bundles and wherein the lead wires are tethered to the nerve bundle by a flexible helical or spirally shaped strain relief tether formed similarly to the electrode. The tether is formed at a point longitudinally spaced from the lead wire to electrode junction and causes the lead wires to be positioned relatively parallel to the electrode from the junction point to the tether. Mechanical forces imparted on the lead wires are absorbed by the flexible tether and underlying nerve bundle rather than at the delicate junction between the electrode and the lead wires.

DESCRIPTION OF THE DRAWINGS

FIG. 1 illustrates an implantable helical electrode incorporating one embodiment of the strain relief tether of the present invention;

FIG. 2 illustrates a second embodiment of a strain relief tether of the present invention.

FIGS. 3 and 4 illustrate yet another embodiment of a strain relief tether of the present invention.

DESCRIPTION OF THE PREFERRED EMBODIMENT

Referring now to the drawings, in FIG. 1 the letter E designates generally an implantable electrode incorporating the present invention. The electrode E as illustrated in FIG. 1, comprises generally a helically shaped, flexible structure implanted around a human nerve bundle N. Electrode E is formed of a flexible biocompatible substrate 10 which is preferably a formed silicone rubber, preshaped in a helical configuration. This construction enables the physician to implant the electrode E by wrapping a first end around the nerve N and twisting the electrode in corkscrew fashion until the full length of the electrode surrounds a selected portion of the nerve bundle N.

Embedded in substrate 10 are the electrode conductor elements 12 and 14 which are preferably formed of very thin platinum ribbon, which in some cases may be only 0.0001 inches thick. These conductor elements are embedded near the inner surface of helical substrate 10 so as to place the conductors in close proximity to nerve bundle N to improve the electrical performance of the electrode. Free ends 16 and 18 of conductor elements 12 and 14 extend from substrate 10 and are attached to surrounding body tissue.

Electrical lead wires 20 and 22 are attached to the conductor elements 12 and 14 at weld joints 24 and 26, respectively. Lead wires 20 and 22 are stainless steel conductors which electrically couple the electrode E to the diagnostic or therapeutic instrument in use. Lead wires 20 and 22 are formed so as to exit the weld points 24 and 26 and lie tangentially to the helical substrate 10 generally parallel to the longitudinal axis of nerve bundle N. This configuration, in combination with the lead wire tether described below greatly reduces the strain imposed by movement or mechanical forces in the lead wires at weld points 24 and 26.

The present invention further includes a tether T which is formed in a helical or spiral configuration resembling the construction of the electrode substrate 10. Tether T includes a flexible, preferably silicone rubber substrate 30, formed having an inner surface which conforms closely to the generally cylindrical outer surface of nerve N. Tether T further includes attachment suture tines 32 and 34 which engage surrounding tissue to position tether T on nerve bundle N. In the preferred embodiment, these portions of tether T closely resemble corresponding portions of electrode E and may be formed using the same manufacturing process.

Tether T further includes a lead wire retaining ring 36, which preferably is formed of flexible, elastic, biocompatible material such as silicone rubber and would be manufactured as an integral part of the lead wire assembly and the tether. Alternatively, long silicone rubber strings or tubes may be used which are tied around the leads after assembly and are an integral part of the tether during the manufacture (see FIG. 2). Retaining ring 36 is essentially a closed ring or loop formed approximately midway along the length of tether T and extending outward therefrom to provide a passageway for lead wires 20 and 22. In this fashion retaining ring 36 maintains lead wires 20 and 22 in an essentially parallel, tangential orientation relative to nerve bundle N. Mechanical forces acting on lead wires 20 and 22 which would otherwise be imparted to weld points 24 and 26 are absorbed by ring 36 and the elastic properties of helical substrate element 30. In this manner, the potential for electrode failure due to lead wire fatigue or weld point discontinuity is greatly reduced. Furthermore, by absorbing mechanical forces in the elastic tether T the risk of nerve damage is also reduced.

Referring now to FIGS. 3 and 4, yet another alternative embodiment of the tether T, designated T' is illustrated. In this embodiment, tether T' includes an essentially spiral shaped substrate 40, which when relaxed has a generally cylindrical inner surface to conform to the outer surface of nerve bundle N. Substrate 40 is formed of biocompatible, flexible material, preferably silicone rubber. Substrate 40 wraps closely around nerve bundle N, in proximity to electrode element E in the same fashion as tether T illustrated in FIG. 1. Tether T' further includes an electrode lead wire retaining ring 42 which is of similar construction and function as ring 36 described above.

The foregoing disclosure and description of the invention are illustrative and explanatory thereof and various changes in the size, shape and materials as well as in the details of the preferred embodiment may be made without departing from the spirit of the invention.

I claim:

1. In an implantable electrode system of the type adapted to provide electrical coupling to a nerve bundle and including an electrode element with an electrical lead wire connected to the electrode element and adapted to be connected to remote medical instruments, a lead wire tether comprising:
    a flexible carrier element adapted for attachment to the nerve bundle; and
    a lead wire retaining ring, attached to said carrier element and adapted to surround a portion of the electrical lead wire,
    wherein said carrier element comprises a helically shaped body adapted to surround a portion of the nerve bundle.

2. A surgically implantable electrode system for providing electrical coupling to a nerve bundle, said system comprising:
    (a) an electrode including:
        an insulating element adapted to be positioned around a portion of the nerve bundle,
        a conductor element mounted with said insulating element, said conductor element being adapted for electrical coupling to the nerve bundle, and
        an electrical lead element coupled to said conductor element; and
    (b) an electrode lead wire tether means for tethering said electrical lead element to the nerve bundle, said tether means comprising a flexible carrier element adapted to surround a portion of the nerve bundle and a lead wire retaining ring attached to said carrier element, and adapted to receive and retain said electrical lead element.

3. The system of claim 2, wherein said flexible carrier element is formed of silicone rubber.

4. The system of claim 2, wherein said lead wire retaining ring is formed of silicone rubber.

5. The system of claim 2, wherein said flexible carrier element comprises a helically shaped element adapted for mounting around a portion of the nerve bundle.

6. The system of claim 2, wherein said flexible carrier element comprises a spirally shaped element adapted for mounting around a portion of the nerve bundle.

* * * * *